United States Patent [19]
Strachan

[11] Patent Number: 5,980,041
[45] Date of Patent: Nov. 9, 1999

[54] POINT OF OBSERVATION TRACKING DEVICE AND EYE FOCUS MEASURING DEVICE

[75] Inventor: John Scott Strachan, Prestonfield, United Kingdom

[73] Assignee: Ferranti Technologies Limited, Oldham, United Kingdom

[21] Appl. No.: 09/029,711

[22] PCT Filed: Sep. 9, 1996

[86] PCT No.: PCT/GB96/02233

§ 371 Date: Nov. 12, 1998

§ 102(e) Date: Nov. 12, 1998

[87] PCT Pub. No.: WO97/08985

PCT Pub. Date: Mar. 13, 1997

[30] Foreign Application Priority Data

Sep. 9, 1995 [GB] United Kingdom .................... 9518477

[51] Int. Cl.⁶ ........................................................ A61B 3/14
[52] U.S. Cl. ................................................................ 351/210
[58] Field of Search ..................................... 351/205, 206, 351/209, 210, 211; 356/354, 355, 356, 349, 359

[56] References Cited

U.S. PATENT DOCUMENTS 4,410,244  10/1983  Remijan .
5,638,176   6/1997  Hobbs et al. ............................ 356/355

FOREIGN PATENT DOCUMENTS

WO 86/02249
A1  4/1986  WIPO .

*Primary Examiner*—George Manuel
*Attorney, Agent, or Firm*—Adams Law Firm, P.A.

[57] ABSTRACT

The invention relates to a point of observation tracking device comprising means (8, 12) for directing light from a holographic element (12) to the retina (4) of a user, and means for tracking the reflection of the light (12, 14) from the retina (4) thereby to provide a signal representative of the point of observation of the eye or eyes of the user.

35 Claims, 2 Drawing Sheets

POINT OF OBSERVATION TRACKING DEVICE AND EYE FOCUS MEASURING DEVICE

This application is a national stage application, according to Chapter II of the Patent Cooperation Treaty. This application claims the priority date of Sep. 9, 1995 for Great Britain Patent Application No. 9518477.6.

FIELD OF THE INVENTION

The invention relates to point of observation tracking devices for use, by way of example, in control systems, psychological research and other applications where information about the point of observation is useful. The invention also relates to devices for measuring eye focus.

BACKGROUND TO THE INVENTION

Various methods for tracking the point of observation, eye position, or point of gaze (which may be regarded as equivalent end-results) have been proposed but commonly these approaches suffer from complexity and consequent high cost, bulkiness or poor performance. Prior methods include attempting to track the muscular movements of the eye with mechanical transducers and various optical techniques.

The optical methods used in the prior art fall into two categories, viz, 1: tracking the position of the pupil; and 2: tracking a highlight from the cornea.

The pupil tracking systems are limited in accuracy by several factors the most important being the poor contrast between the iris and the pupil, particularly with dark coloured irises, which reduces the resolution with which a camera can define the pupil boundary. Secondly the iris commonly has an irregular dark border at the edge of the pupil which further degrades accuracy. Thirdly the relative motion of the pupil is not related to an external reference physically aligned with the user's head and so extrapolation of the pupil position to determine the point of observation yields poor repeatability.

The corneal highlight systems suffer from high degree of variation in corneal profiles both between individuals and from time to time in the same individual due to variations in eyeball pressure due to air pressure. The nature of the corneal highlight apparatus also causes further variations and poor repeatability since small changes in the relationship of the illumination source to the cornea drastically affect the position of the highlight.

Preferred embodiment of the present invention aim to obviate or overcome disadvantages of the prior art, whether referred to herein or otherwise.

SUMMARY OF THE INVENTION

According to the present invention in a first aspect, there is provided a point of observation tracking device comprising means for directing light from a holographic element to the retina of a user, and means for tracking the reflection of the light from the retina thereby to provide a signal representative of the point of observation of the eye or eyes of the user.

In this specification, unless the context requires otherwise the term light is used in its widest sense including the full range of electromagnetic wavelengths. In particular, it is not to be limited to the range of visible wavelengths.

Suitably, a source of illumination is provided to produce the light to be directed to the retina.

Suitably, the source of illumination comprises a controlled source. More suitably, it comprises a source of light outside the human visible spectrum, such as infra-red light.

The illumination source should be of equal intensity across the entire field of view of the camera. The illumination sphere or holographic diffusing optic should also have a focal angle of dispersion equal to the focal angle of the camera lens. These criteria ensure that good retro-reflection is obtained from the retina. Long wavelength light sources can be used so as substantially to eliminate night vision restrictions.

Preferably, the light directed to the retina comprises a holographic image. Suitably, the holographic image varies in focal length over space. Suitably, the holographic image comprises a plurality of lines which conveniently are regularly spaced. A suitable holographic image is a hemisphere or part thereof, typically formed from a grid of lines.

The holographic element preferably is a transmission hologram.

Suitably, the tracking means comprises a sensor and means for directing light reflected from the retina to the sensor. Conveniently, the sensor comprises an array of light sensitive devices and typically the sensor will be coupled to a data processor which normally will be a computer for analysis of the results and production of a signal representative of the point of observation of the eye. The data processor may comprise means for determining the intensity of light across the sensor, means for determining the centre of the reflected light on the sensor and means for generating a signal therefrom. The sensor may comprise a charge coupled device camera semi-conductor device.

Suitably, the reflected light directing means comprises an optical element which preferably is a holographical optical element. Advantageously the holographic optical element of the reflected light direct means is combined with the holographic optical element directing light to the retina.

Advantageously the reflected light directing means directs the reflected light towards the tracking means. It is noted that the focus at the sensor of the tracking means need not be complete.

Suitably, the first aspect of the invention is modified according to the second aspect of the invention.

According to the present invention in a second aspect, there is provided an eye focus measuring device comprising means for directing a pattern light to the retina of a user, which light pattern varies in space, and means for measuring the intensity of light reflected from the retina of the user, thereby to measure the focus of the eye and means for generating a signal representative of the focus of the eye.

Suitably, the light intensity measuring means comprises a sensor and a rectilinear holographical optical element for directing the light from the retina to the sensor.

The second aspect of the invention may be modified according to the first aspect of the invention.

BRIEF DESCRIPTION OF THE DRAWINGS

The present invention will now be described, by way of example only, with reference to the drawings that follow; in which.

DESCRIPTION OF THE PREFERRED EMBODIMENTS

Figure 1:
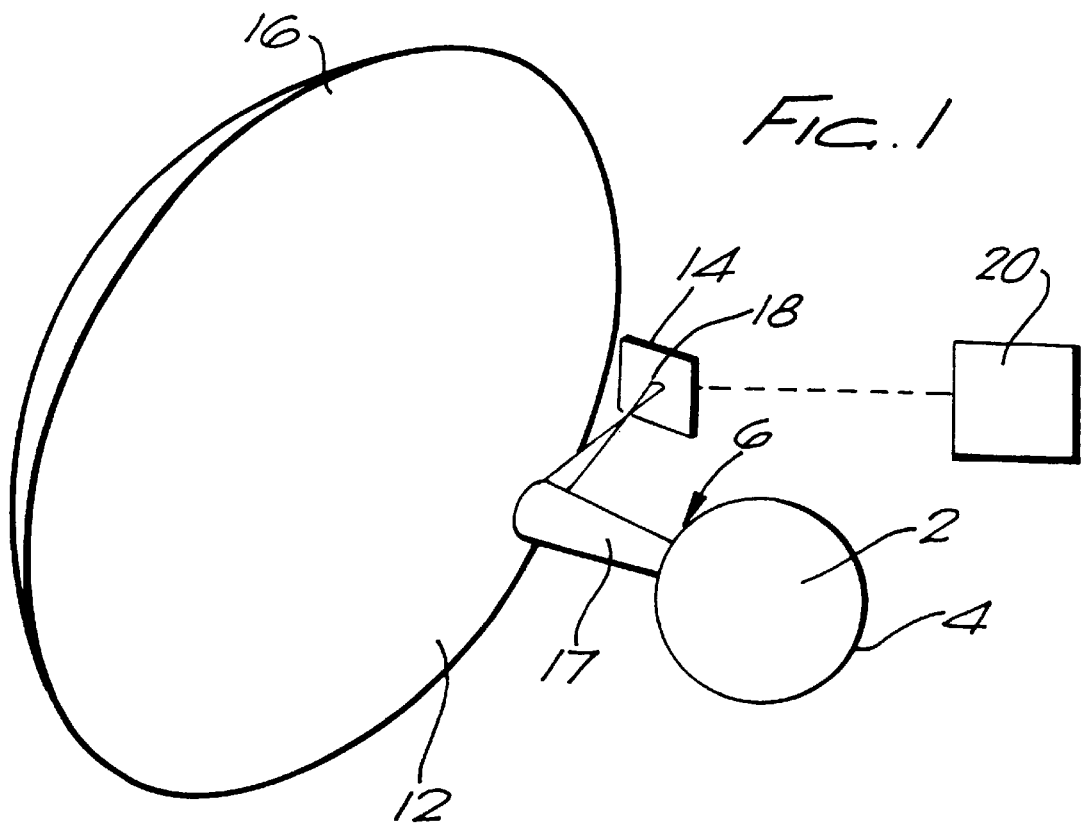
FIG. 1 shows a schematic perspective view of the overall arrangement of a device according to the present invention.
Figure 2:
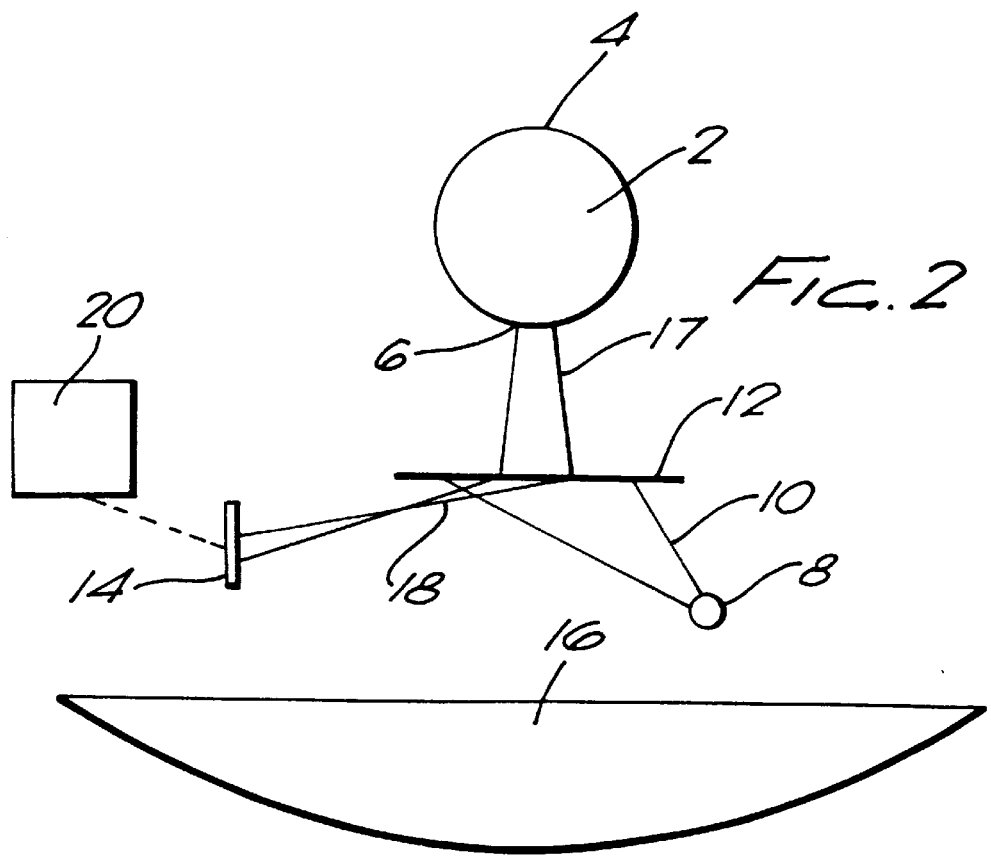
FIG. 2 is a schematic operational diagram of the device shown in FIG. 1.

Referring to FIGS. 1 and 2 of the drawings that follow, there is shown schematically a device according to the present invention.

In FIG. 1, there is shown a human eyeball 2 including a retina 4 and an eye lens 6. An illumination source 8 is shown with light transmitted therefrom indicated at 10. Between the eye 2 and illumination source 8 is a holographic optical element ("HOE") 12 and spaced therefrom a sensor device 14 coupled to a signal processor (microprocessor) 20. The sensor device 14 is located outside the field of view of the user. Also shown in the Figures is a holographic image of a hemisphere 16, the origin and purpose of which is set out below.

A transmission holographic image of the interior of a diffusely reflecting hemisphere or partial hemisphere 16 is prepared in the conventional manner familiar to those skilled in the art. The transmission hologram is combined with a second hologram which is a holographic optical element (HOE) in the form of a lens to form the combined HOE 12. The second HOE is formed to focus the light falling on the HOE 12 to a point to the side of the HOE 12. The second HOE may be made by optical methods or, preferably, it can be generated directly by computer calculating the fringe structure of the second HOE in the manner familiar to those skilled in the art and widely published. A suitable program for generating such a HOE is marketed by ZEMAX. This optically recorded or computer generated second HOE is then reproduced on suitable medium such as a photopolymer or a metal stamping tool for mass production as a pressed hologram similar to those used for credit card anti-forgery symbols.

The image hologram and the HOE may be laminated together or they may be holographically copied on to a single holographic plate for conversion into a stamping tool or copied directly to photopolymer.

Photopolymer holograms are currently preferred for the purpose since they are capable of higher efficiency.

Silver halide holograms would also work but would be relatively low in transparency and therefor less useful.

The operation of the device shown in FIGS. 1 and 2 will now be explained. Illumination source 8 directs a narrow bandwidth of light such as that coming from a laser on to the holographic element 12 which generates the image of a bright evenly illuminated interior of a hemisphere 16. The light from this hemisphere 16 passes through the eye lens 6 and reflects from the retina 4. The light 17 reflected from retina 4 is partially focused by the eye lens 6 before passing through the HOE 12 and becomes a beam 18 focused on or about sensor chip 14. Wherever the eye looks the light from the hemisphere will be collected and reflected from the retina 4. The resultant beam 17 and 18 is projected on the surface of sensor device 14.

In the case of a computer generated HOE 12 the lens formed by the HOE 12 may be rectilinear having a variation in focal length across the surface of the HOE 12. Thus it may be capable of compensating for the different focal paths and lengths as the eye moves and beam 18 changes its angle.

A microprocessor based computer 20 is coupled to the sensor 14 to analyse the data and provide an output signal indicative of the point of observation and focus of the eye.

In this case the device may provide further information if the illumination hemisphere 16 has a pattern such as a grid of lines on its surface, which is preferred. This grid of lines will be imaged on the retina 4 but will have a definition dependent on the relative distance the eye lens 6 is currently focusing and the distance of the holographic image of the illumination hemisphere 16. Thus the projection of these grid lines from the retina 4 on the sensor device 14 will produce an image of the grid lines with a definition depending on the eye's focus. The focus of the HOE 12 may be arranged such that the full range of eye focus from close focus to infinity tends to but never reaches perfect focus on the sensor device 14.

Conveniently, the sensor device 14 comprises a charge coupled device camera semiconductor device (chip). In such a case simple analysis of the image of each grid line across a number of camera pixels will enable the actual focus of the eye to ascertained. The light can be focused to a point in front of or behind the sensor 14. In the simplest form this analysis would measure they grey scale value for each pixel across a line perpendicular to the image of the grid line from the holographic hemisphere image 16 and produce a curve of intensity from the resulting values. The total width of the defocused line image above a predetermined grey scale value would then be compared to a constant value representing the width of a focused line in pixels. The resulting value would be a function of the relative focus of the eye to the focus represented by the constant.

This simple analysis is adequate to demonstrate the principle of focus measurement with the invention though many mathematical algorithms familiar to those skilled in the art may be used to exploit the data provided by the device. Some algorithms that make use of spatial frequency Fourier transforms would work best if the focus of the HOE 12 were set to a median between infinity and close focus rather than towards one or other extreme as would be the case for the simple algorithm described here.

The projected reflection of the retina 4 on to sensor device 14 is bounded by the pupil aperture (not shown specifically) behind the eye lens 6. The pupil is rarely perfectly circular and so the projected spot of light will form a slight irregular image on the sensor device 14. Since sensor device 14 in the form of a camera chip consists of a large array of charge coupled devices (or alternatively photodiodes) forming picture elements or "pixels", the image spot will fall fully on some pixels and partially on others. Those pixels at the perimeter of the spot of light can and will have a grey scale value falling somewhere between the bright area at the centre of the spot and the dark area beyond the perimeter. They grey scale value can be used to represent the proportion of the pixel exposed to the light. Thus the perimeter of the spot can be determined to a resolution greater than the resolution defined by the number of pixels in the image. Further the centre of the spot can be calculated irrespective of the irregularity of the perimeter by integrating the values of the grey scales across each line of pixels in the image of the spot and differentiating twice to find the centre of the curve or by simply using the grey scale values at either end of the line to adjust the centre determined from dividing the bright pixels by two. This could be done by adding together the grey scale values of the pixels at either end of the line and performing the following simple calculation:

$$V = \frac{a}{(a+b)} \quad U = \frac{N}{2} \quad P = U + V$$

Where a is the pixel partially illuminated at the left side of the spot; b is the pixel partially illuminated at the right side of the spot and N is the number of pixels fully illuminated by the spot. The value P is used to determine the distance in pixels and fractions of a pixel from a to the centre of the row of pixels in the spot image. The vertical centre can be determined by a similar process for each vertical line of pixels in the same way as the above process determines the horizontal centre. A curve can then be plotted with all the values of P and differentiated to determine the centre in each axis.

In practice this process may be simplified by directly differentiating the analogue voltage curve delivered from the D to A converter used in most camera chips after applying a low pass filter set at a frequency value slightly greater than the frequency defined by taking the reciprocal of the number of pixels in a typical spot width multiplied by the sampling time of each pixel.

The holographic illumination hemisphere 16 may be replaced with a further HOE (not shown) that simply focuses the source 8 to a point behind the retina 14. This arrangement could still exploit the focus measurement potential of the system by arranging for the illumination source 8 to project a grid of lines through the HOE. This embodiment is not preferred because the source 8 may accidentally be focused on to a spot on the retina 4 during the removal of the device from the user's head. Thus if the source 8 was powerful enough, damage to the retina 4 may result. Conversely, the illumination hemisphere can never be focused to a spot and so although the reflected light from the retina 4 can be just as bright from source 8 it can never be focused so that the power per square millimeter exceeds the safe limits for the retina 4. This is an important advantage over the prior art devices that propose the use of corneal highlight as a means of tracking the eye position. Such devices need to use point source illumination and some propose the use of lasers for the purpose.

The source of illumination 8 is preferably infra red and beyond the range of human vision so that the illumination hemisphere is not perceived by the user. Thus provided the holographic elements are reasonably transparent as is the case with a photopolymer hologram and to a reasonable extent with a pressed hologram the view of the eye is unobstructed by the device. Thus the device may be used to determine the direction of the eyes view relative to the world if means are provided to determine the position of the device itself or if the device is fixed relative to the world.

Figure 3:
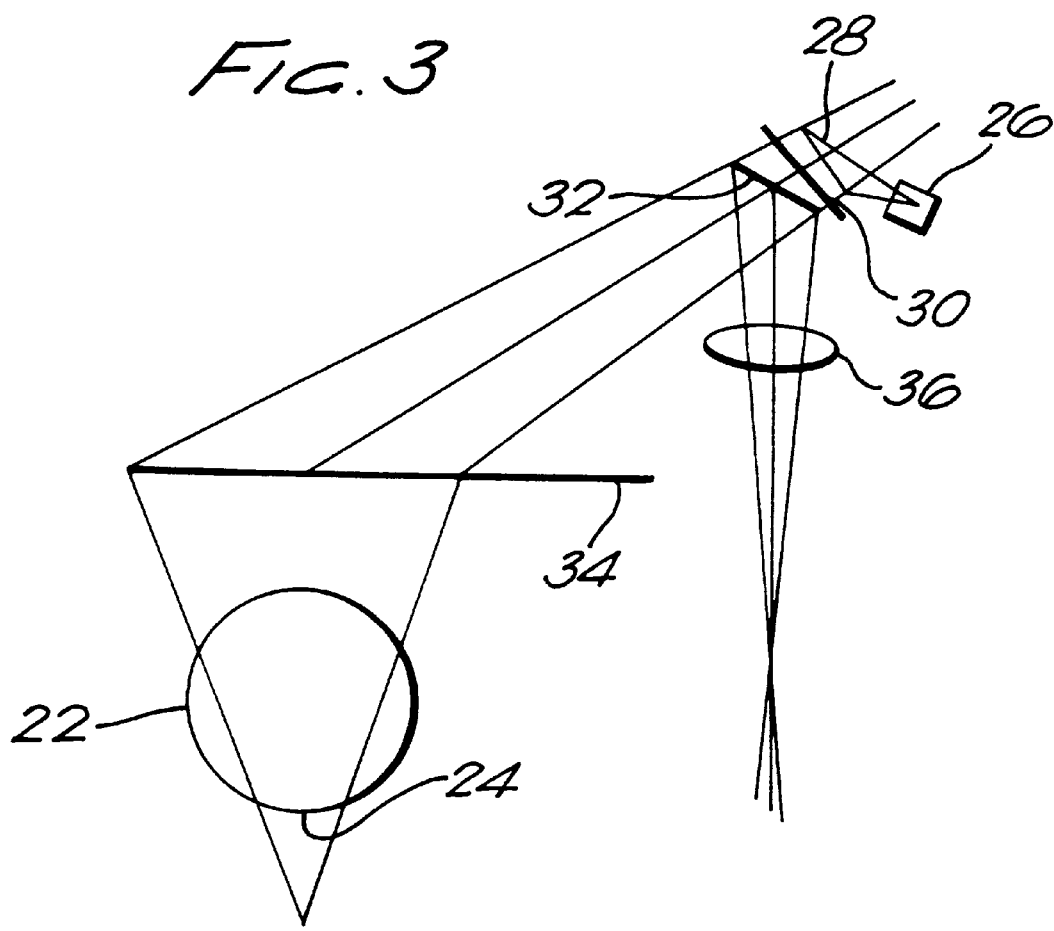
FIG. 3 is a schematic operational diagram of another device according to the present invention.

Referring to FIG. 3 of the drawings that follow, there is shown a second embodiment of the present invention. The second embodiment is sufficiently similar to the first embodiment described above that the skilled reader will only require a brief description thereof which follows.

In FIG. 3, there is shown an eye 22 of a user, the eye 22 including a retina 24. The device according to the present invention comprises a coherent infra-red light emitting laser 26, the output of which is directed to an illumination hologram 28. The light from the laser 26 is redirected by hologram 28 through a light guide film 30, a beam splitter 32 (which from this direction does not split the light beam) to a holographic optical element 34 simulating a lens which redirects and focuses the light to the user's eye 22.

Light reflected from the user's retina 24 is redirected by holographic optical element 34 to the beam splitter 32. The beam splitter 32 re-directs the reflected light through a lens 36 to a detector (not shown).

Thus, there is a first hologram 28 to generate the illumination sphere and a second hologram 34 to act as a lens.

The configuration of the second embodiment makes use of a second holographic optical element in front of the eye. This swings round the axis of the optical frame ("de-levers") and thus removes the need for the electronics in the sensor detector apparatus to subtract 45 degrees from the cosine correction. It provides a wider field of view and of course also prevents the cosine approaching 90 degrees where the resolution of the camera is limited. This optical arrangement requires the use of a laser source for best performance as the holographic focusing efficiency is poor for a wide band source.

The precision advantage of this optical system is not likely to be needed in most applications. The primary source of error for aiming and control arises from the eyes micro saccade behaviour when concentrating on a single object. So, for most applications intelligent software will make use of the data to derive the viewpoint from averaging of the saccades and the low resolution noisy data from a non de-levered system.

This configuration is applicable, in particular, to high resolution applications such as medical and/or psycho-optical areas.

Figure 4:
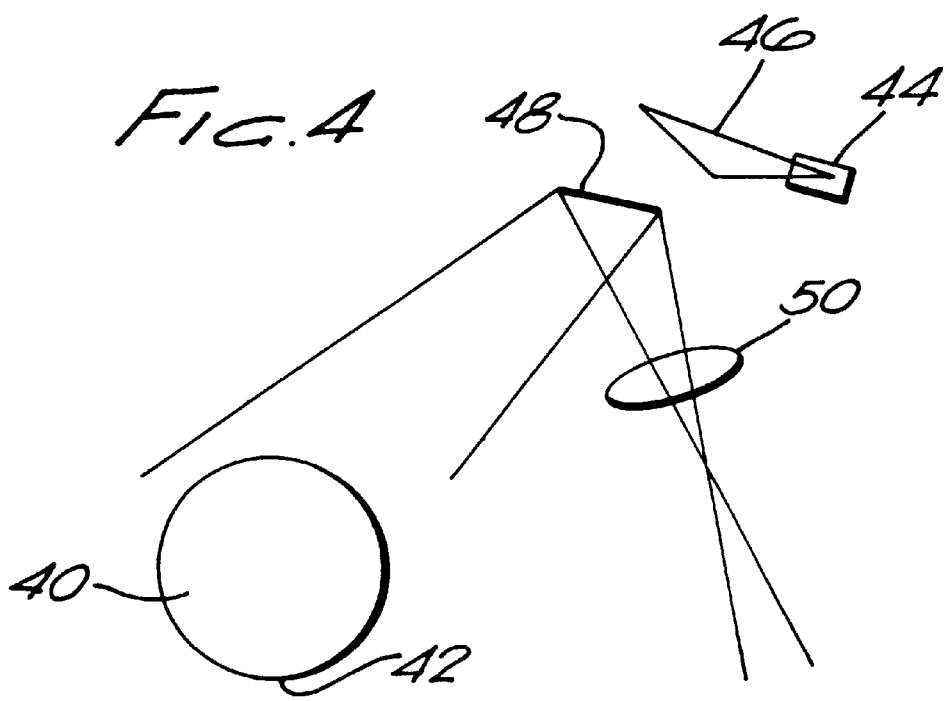
FIG. 4 is a schematic operational diagram of a further device according to the present invention.

Referring to FIG. 4 of the drawings that follow, there is shown a third embodiment of the present invention in relation to which the skilled reader will only require a brief description which follows.

In FIG. 4 there is shown an eye 40 of a user, the eye 40 including a retina 42.

The device according to the invention comprises an infra-red light emitting diode 44 the output of which is directed to an illumination hologram 46. The incident light is redirected from the illumination hologram 46 through a beam splitter 48 to the user's eye 40. Light reflected from the retina 42 of the eye 40 towards the beam splitter 48 is redirected through a lens 50 to a detector (not shown).

In the second and third embodiments of the present invention described above, the illumination holograms 28, 46 respectively generate the holographic image (identified by numeral 16 in relation to the first embodiment to be directed to the user's eye.

For applications that require fast response and high intrinsic accuracy of current eye position such as medical research and possibly some military applications the de-levered system of the third embodiment should be used. In applications where very high instantaneous accuracy is needed the de-levering hologram provides an advantage in the order of a factor of ten.

The device of the third embodiment is useful for moderate resolution applications such as military aiming, switch control, computing etc. It has the advantages that there is no obstruction over the eye, no laser is required and it is less complex. However, it does suffer from the disadvantages that there is a relatively small detectable range of motion due to the cosine on the left field of view and lower overall angle of trackable view. Additional advantages of not using a de-levered system where the resolution allows are that no laser is required saving several pounds in cost and of course not requiring special licences or labels for sale.

If the device is mounted for example on a pair of spectacles (not shown) then means known to those skilled in the art may be provided to determine the position of the device relative to the world and most particularly the elements that the device must determine the wearer is observing. One means of providing such data is to have a second camera chip mounted on the device. This second camera chip would have a wide angle lens which may also be holographic. It may also use a filter to eliminate other sources of light not at the wavelength of the source(s) of illumination. A pair of illumination sources at a specific (preferably invisible) wavelength are mounted on a structure within the field of view such as a computer monitor. The image of these illumination sources will be projected on to the camera chip and for example, by use of the means described above for determination of the centre of the eye spot, the position of these illumination sources may be determined on the camera chip and thus knowing the nature of the camera lens and the separation and orientation of the pair of illumination sources it is a simple matter to determine the position of the device relative to the illumination sources. In one preferred embodiment described by way of example the lens is designed to image the edges of the photodiode array in a wide angle mode and the centre of the array at in a narrow angle mode. This allows relatively high precision of determination of position when the wearer's head is pointing directly towards the point sources of light and a relatively low precision when the head is turned away from the direction of the point sources of light.

One advantageous feature of the device relative to the prior art is that since the spot projected from the reflection of the illumination hemisphere by the retina represents in a real sense the reciprocal of the image plane of the retina, the device accurately tracks the point of observation rather than extrapolating from the corneal reflection or the pupil image. Another important feature is that the contrast obtainable from the image of the infra red reflection of the retina is stable and independent of eye colour the contrast may be set to utilise the full range of the camera chips sensitivity and thus exploit the greatest number of grey scale levels thus increasing the accuracy.

Clearly the system can be manufactured using conventional rather than holographic optics, but in general the advantages of light weight and the ease with which a holographic optical element can focus the light from the retina on to a camera chip in a position that does not obstruct the field of view without the need for intermediate semi silvered mirrors or similar devices, suggests that in general the device would be exploited in the embodiment described by way of example above.

The holographic image could, alternatively, be a plane, sphere, partial sphere or other suitable image.

The lens of the camera in which camera chip 14 is located can have two focal lengths so that one focal length images one part of the photosensor array and the other focal length images a second part of the photosensor array. This can be a long focal length imaging on the centre of the sensor array and a short focal length imaging on the remainder.

Although not referred to above, it will be appreciated that the device will include means for its mounting on a user.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

I claim:

1. A point of observation tracking device comprising a source of illumination, means for directing light from the source of illumination via a holographic element to the retina of a user, and means for tracking the reflection of the light from the retina thereby to provide a signal representative of the point of observation of the eye or eyes of the user for detection by a camera, whereby the holographic element is configured such that the source of illumination is of equal intensity across substantially the entire effective field of view of the camera and such that the light directed from the holographic optical element has a focal angle of dispersion equal to the focal angle of the camera lens.

2. A point of observation tracking device according to claim 1, in which the source of illumination comprises a controlled source.

3. A point of observation tracking device according to claim 2, in which the source of illumination comprises a source of light outside the human visible spectrum.

4. A point of observation tracking device according to claim 1, in which the light directed to the retina comprises a holographic image.

5. A point of observation tracking device according to claim 4, in which the holographic image varies in focal length over space.

6. A point of observation tracking device according to claim 5, in which the holographic image comprises a plurality of lines.

7. A point of observation tracking device according to claim 6, in which the lines are regularly spaced.

8. A point of observation tracking device according to claim 4, in which the holographic image is a hemisphere or part thereof.

9. A point of observation tracking device according to claim 1, in which the holographic element is a transmission hologram.

10. A point of observation tracking device according to claim 1, in which the tracking means comprises a sensor and means for directing light reflected from the retina to the sensor.

11. A point of observation tracking device according to claim 10, in which the sensor comprises an array of light sensitive devices.

12. A point of observation tracking device according to claim 10, in which the sensor is coupled to a data processor.

13. A point of observation tracking device according to claim 12, in which the data processor comprises means for determining the intensity of light across the sensor, means for determining the centre of the reflected light on the sensor and means for generating a signal therefrom.

14. A point of observation tracking device according to claim 10, in which the sensor comprises a charge coupled device camera semi-conductor device.

15. A point of observation tracking device according to claim 10, in which the reflected light directing means comprises an optical element.

16. A point of observation tracking device according to claim 15, in which the optical element is a holographical optical element.

17. A point of observation tracking device according to claim 16, in which the holographic optical element of the reflected light direct means is combined with the holographic optical element directing light to the retina.

18. A point of observation tracking device according to claim 10, in which the reflected light directing means directs the reflected light towards the tracking means.

19. A point of observation tracking device according to claim 1, further comprising means for measuring light intensity and means for generating a signal according to the degree of focus of light impinging on the tracking means.

20. A point of observation tracking device according to claim 19, in which the light intensity measuring means comprises a sensor and a rectilinear holographical optical element for directing the light from the retina to the sensor.

21. An eye focus measuring device comprising means for directing a pattern of light from a source of illumination to the retina of a user through a holographic element, which light pattern varies in space, and means for measuring the intensity of light reflected from the retina of the user which measuring means includes a camera, in which for detection by a camera, whereby the holographic element is configured such that the source of illumination is of equal intensity across substantially the entire effective field of view of the camera and such that the light directed from the holographic optical element has a focal angle of dispersion equal to the focal angle of the camera lens, thereby to measure the focus of the eye and means for generating a signal representative of the focus of the eye.

22. An eye focusing measuring device according to claim 21, in which the light intensity measuring means comprises a sensor and a rectilinear holographical optical element for directing the light from the retina to the sensor.

23. An eye focusing measuring device according to claim 21 further comprising means for directing light to the retina of a user, and means for tracking the reflection of the light from the retina thereby to provide a signal representative of the point of observation of the eye or eyes of the user.

24. An eye focusing measuring device according to claim 23, in which the tracking means comprises a sensor and means for directing light reflected from the retina to the sensor.

25. An eye focusing measuring device according to claim 24, in which the sensor comprises an array of light sensitive devices.

26. An eye focusing measuring device according to claim 25, in which the sensor is coupled to a data processor.

27. An eye focusing measuring device according to claim 26, in which the data processor comprises means for determining the intensity of light across the sensor, means for determining the centre of the reflected light on the sensor and means for generating a signal therefrom.

28. An eye focusing measuring device according to any one of claim 24, in which the sensor comprises a charge coupled device camera semi-conductor device.

29. An eye focusing measuring device according to claim 21, in which the source of illumination comprises a controlled source.

30. An eye focusing measuring device according to claim 21, in which the source of illumination comprises a source of light outside the human visible spectrum.

31. An eye focusing measuring device according to claim 21, in which the light directed to the retina comprises a holographic image.

32. An eye focusing measuring device according to claim 31, in which the holographic image varies in intensity over space.

33. An eye focusing measuring device according to claim 32, in which the holographic image comprises a plurality of lines.

34. An eye focusing measuring device according to claim 33, in which a holographic image is a hemisphere or part thereof.

35. An eye focusing measuring device according to claim 21, in which the light is directed to the retina by a holographic element which preferably is a transmission hologram.

* * * * *